United States Patent
Liu et al.

(10) Patent No.: US 12,018,061 B2
(45) Date of Patent: Jun. 25, 2024

(54) CHIMERIC ENDOCYTIC RECEPTORS AND METHOD OF USE THEREOF

(71) Applicant: ST PHI THERAPEUTICS CO., LTD., Zhejiang (CN)

(72) Inventors: Steven Lingfeng Liu, Seattle, WA (US); Wenting Zhong, Wuping (CN)

(73) Assignee: ST PHI THERAPEUTICS CO., LTD., Zhejiang (CN)

( * ) Notice: Subject to any disclaimer, the term of this patent is extended or adjusted under 35 U.S.C. 154(b) by 779 days.

(21) Appl. No.: 16/813,417

(22) Filed: Mar. 9, 2020

(65) Prior Publication Data

US 2020/0283495 A1  Sep. 10, 2020

Related U.S. Application Data

(60) Provisional application No. 62/919,382, filed on Mar. 8, 2019.

(51) Int. Cl.
| | |
|---|---|
| *C07K 14/705* | (2006.01) |
| *A61K 35/15* | (2015.01) |
| *A61K 35/17* | (2015.01) |
| *C07K 14/735* | (2006.01) |
| *C07K 19/00* | (2006.01) |
| *C12N 5/0783* | (2010.01) |
| *C12N 5/0786* | (2010.01) |
| *C12N 15/86* | (2006.01) |

(52) U.S. Cl.
CPC ............ *C07K 14/705* (2013.01); *A61K 35/15* (2013.01); *A61K 35/17* (2013.01); *C07K 14/70517* (2013.01); *C07K 14/70521* (2013.01); *C07K 14/70532* (2013.01); *C07K 14/70535* (2013.01); *C07K 14/70578* (2013.01); *C07K 19/00* (2013.01); *C12N 5/0636* (2013.01); *C12N 5/0645* (2013.01); *C12N 15/86* (2013.01); *C07K 2317/24* (2013.01); *C07K 2317/56* (2013.01); *C07K 2319/01* (2013.01); *C07K 2319/03* (2013.01); *C12N 2510/00* (2013.01); *C12N 2740/15043* (2013.01)

(58) Field of Classification Search
CPC ............ C07K 14/7051; C07K 2319/03; C07K 2317/622; C07K 2319/33; C07K 2319/02; C07K 2317/24; C07K 2317/53; C07K 14/70535; C07K 19/00; C07K 14/705; C07K 2317/31; C07K 2319/00; C07K 2317/56; A61K 39/3955; A61K 39/395; A61K 2039/505; C12N 5/0645; C12N 5/0636

See application file for complete search history.

(56) References Cited

U.S. PATENT DOCUMENTS

| | | | | |
|---|---|---|---|---|
| 2017/0151281 | A1* | 6/2017 | Wagner | .................. C07K 16/30 |
| 2018/0244748 | A1* | 8/2018 | Gill | ......................... A61P 37/02 |

FOREIGN PATENT DOCUMENTS

| | | | |
|---|---|---|---|
| WO | WO-2016210293 A1 | * | 12/2016 |
| WO | WO-2017177217 A2 | * | 10/2017 |
| WO | WO-2018064076 A1 | * | 4/2018 |

OTHER PUBLICATIONS

Caratelli et al. Fcgamma chimeric receptor-engineered T cells: methodology, advantages, limitations, and clinical relevance. Front Immunol 8: 457, 2017.*
Clemenceau et al. Antibody-dependent cellular cytotoxicity (ADCC) is mediated by genetically modified antigen-specific human T lymphocytes. Blood 107(12): 4669-4677, 2006.*
Clemenceau et al. In vitro and in vivo comparison of lymphocytes transduced with a human CD16 or with a chimeric antigen receptor reveals potential off-target interactions due to the IgG2 CH2-CH3 CAR-spacer. J Immunol Res vol. 2015: 482089, 2015.*
Eshhar et al. Specific activation and targeting of cytotoxic lymphocytes through chimeric single chains consisting of antibody-binding domains and the γ or ξ subunits of the immunoglobulin and T-cell receptors. Proc Natl Acad Sci USA 90: 720-724, 1993.*
Hamdan et al. The diverse functions of the ubiquitous Fcgamma receptors and their unique constituent, FcRgamma subunit. Pathogens 9: 140, Feb. 2020.*
Heuser et al. T-cell activation by recombinant immunoreceptors: impact of te intracellular signalling domain on the stability of receptor expression and antigen-specific activation of grafted T cells. Gene Therapy 10: 1408-1419, 2003.*

(Continued)

*Primary Examiner* — Bridget E Bunner
(74) *Attorney, Agent, or Firm* — Jun He Law Offices P.C; James J. Zhu

(57) ABSTRACT

The invention discloses chimeric endocytic receptor CER-based constructs for activating and regulating immune response, and method for using the same. The CER-based constructs are based on the structure of FcγRI/γ chain and incorporate high-affinity binding domain from receptors or antibodies shown to uptake specific antigen and present the antigen to T cells or B cells to initiate the antigen-specific immune response, Such design has the ability to transform native monocytes or T cells to CER-expressing monocytes (CER-M) or CER-expressing T cells (CER-T) in recognizing and uptake the target antigen and activate subsequent immune responses. Such engineered CER-M or CER-T can be used to treat tumor, viral diseases and autoimmune diseases directly. The endocytosis process with involvement of FcR-γ may enhance and coordinate T cell activation in combination with T cell activation by other types of constructs such as CAR.

17 Claims, 6 Drawing Sheets

Specification includes a Sequence Listing.

(56) References Cited

OTHER PUBLICATIONS

Indik et al. Insertion of cytoplasmic tyrosine sequences into the nonphagocytic receptor FcgammaRIIB establishes phagocytic function. Blood 83(8): 2072-2080, 1994.*
Indik et al. Structure/function relationships of Fcγ receptors in phagocytosis. Sem Immunol 7: 45-54, 1995.*
Kershaw et al. Supernatural T cells: genetic modification of T cells for cancer therapy. Nature Rev 5: 928-940, 2005.*
Kim et al. Fcγ receptor transmembrane domains: role in cell surface expression, γ chain interaction, and phagocytosis. Blood 10(11): 4479-4484, 2003.*
Sadelain et al. The promise and potential pitfalls of chimeric antigen receptors. Curr Opin Immunol 21: 215-223, 2009.*
Strohl et al. Bispecific T-cell redirection versus chimeric antigen receptor (CAR)-T cells as approaches to kill cancer cells. Antibodies 8: 41, 2019.*
Wang et al. A T cell-independent antitumor response in mice with bone marrow cells retrovirally transduced with an antibody/Fc-γ chain chimeric receptor gene recognizing a human ovarian cancer antigen. Nature Med 4(2): 168-172, 1998.*

* cited by examiner

FIG. 2A: scFv | Hinge | FcγRI TM/ICD | 2A | FCRγ chain

FIG. 2B: Receptor/ligand ED | Hinge | FcγRI TM/ICD | 2A | FCRγ chain

FIG. 2C: scFv | Hinge | FcγRI TM/ICD | 2A | FCRγ chain | 2A | Costimulatory ligand FIG. 2D: Receptor/ligand ED | Hinge | FcγRI TM/ICD | 2A | FCRγ chain | 2A | Costimulatory ligand FIG. 2E: scFv | Hinge | FcγRI TM/ICD | 2A | FCRγ chain | 2A | TAA scFv | Hinge/TM | CD28/4-1BB | CD3Z FIG. 2F: Receptor/ligand ED | Hinge | FcγRI TM/ICD | 2A | FCRγ chain | 2A | TAA scFv | Hinge/TM | CD28/4-1BB | CD3Z

FIG. 2

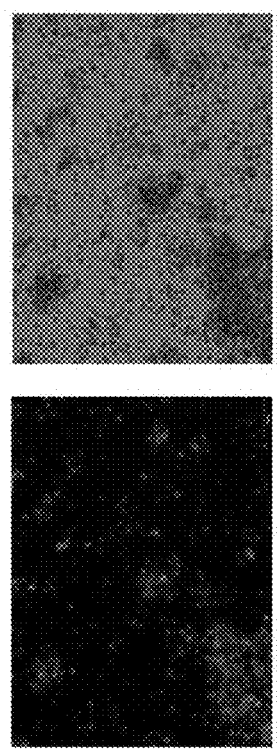
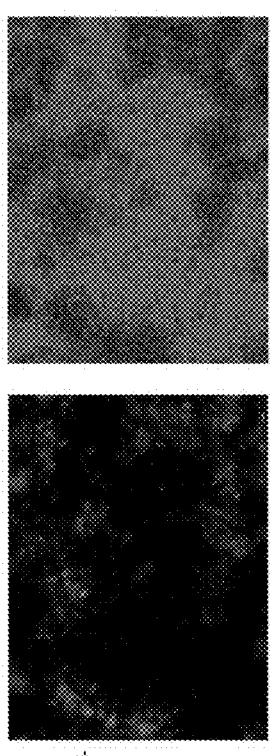
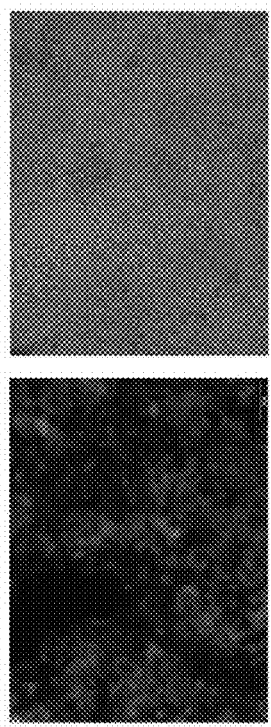
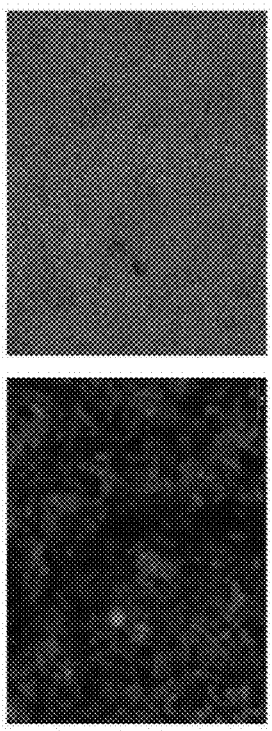
E:T=1:10 for all
FIG. 5A CONTROL
FIG. 5B Anti-AFP CER-T
FIG. 5C Anti-GPC3 CAR-T
FIG. 5D Anti-AFP-CER/anti-GPC3-CAR-T
FIG. 5

SEQUENCE LISTING

<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: synthetic sequence

<400> SEQUENCE: 1

Glu Pro Lys Ser Cys Asp Lys Thr His Thr Cys Pro Pro Cys Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: syntheti sequence

<400> SEQUENCE: 2

Glu Arg Lys Cys Cys Val Glu Cys Pro Pro Cys Pro
1               5                   10

```
<210> SEQ ID NO 3
<211> LENGTH: 15
<212> TYPE: PRT
<213> ORGANISM: Artificial Sequence
<220> FEATURE:
<223> OTHER INFORMATION: syntheti sequence

<400> SEQUENCE: 3

Glu Pro Lys Ser Cys Asp Thr Pro Pro Cys Pro Pro Cys Pro
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: syntheti sequence

<400> SEQUENCE: 4

Glu Ser Lys Tyr Gly Pro Pro Cys Pro Ser Cys Pro
1               5                   10

<210> SEQ ID NO 5
<211> LENGTH: 36
<212> TYPE: PRT
<213> ORGANISM: Artificial Sequence
<220> FEATURE:
<223> OTHER INFORMATION: syntheti sequence

<400> SEQUENCE: 5

Leu Gln Val Leu Gly Leu Gln Leu Pro Thr Pro Val Trp Phe His Val
1               5                   10                  15

Leu Phe Tyr Leu Ala Val Gly Ile Met Phe Leu Val Asn Thr Val Leu
                20                  25                  30

Trp Val Thr Ile
            35

<210> SEQ ID NO 6
<211> LENGTH: 61
<212> TYPE: PRT
<213> ORGANISM: Artificial Sequence
<220> FEATURE:
<223> OTHER INFORMATION: syntheti sequence

<400> SEQUENCE: 6

Arg Lys Glu Leu Lys Arg Lys Lys Lys Trp Asp Leu Glu Ile Ser Leu
1               5                   10                  15

Asp Ser Gly His Glu Lys Lys Val Ile Ser Ser Leu Gln Glu Asp Arg
                20                  25                  30

His Leu Glu Glu Glu Leu Lys Cys Gln Glu Gln Lys Glu Glu Gln Leu
            35                  40                  45

Gln Glu Gly Val His Arg Lys Glu Pro Gln Gly Ala Thr
    50                  55                  60

<210> SEQ ID NO 7
<211> LENGTH: 21
<212> TYPE: PRT
<213> ORGANISM: Artificial Sequence
<220> FEATURE:
<223> OTHER INFORMATION: syntheti sequence

<400> SEQUENCE: 7

Gly Ser Gly Glu Gly Arg Gly Ser Leu Leu Thr Cys Gly Asp Val Glu
1               5                   10                  15
```

```
Glu Asn Pro Gly Pro
            20

<210> SEQ ID NO 8
<211> LENGTH: 22
<212> TYPE: PRT
<213> ORGANISM: Artificial Sequence
<220> FEATURE:
<223> OTHER INFORMATION: syntheti sequence

<400> SEQUENCE: 8

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 9
<211> LENGTH: 23
<212> TYPE: PRT
<213> ORGANISM: Artificial Sequence
<220> FEATURE:
<223> OTHER INFORMATION: syntheti sequence

<400> SEQUENCE: 9

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 10
<211> LENGTH: 25
<212> TYPE: PRT
<213> ORGANISM: Artificial Sequence
<220> FEATURE:
<223> OTHER INFORMATION: syntheti sequence

<400> SEQUENCE: 10

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 11
<211> LENGTH: 86
<212> TYPE: PRT
<213> ORGANISM: Artificial Sequence
<220> FEATURE:
<223> OTHER INFORMATION: syntheti sequence

<400> SEQUENCE: 11

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
            85
```

<210> SEQ ID NO 12
<211> LENGTH: 288
<212> TYPE: PRT
<213> ORGANISM: Artificial Sequence
<220> FEATURE:
<223> OTHER INFORMATION: syntheti sequence

<400> SEQUENCE: 12

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

<210> SEQ ID NO 13
<211> LENGTH: 329
<212> TYPE: PRT
<213> ORGANISM: Artificial Sequence
<220> FEATURE:
<223> OTHER INFORMATION: syntheti sequence

<400> SEQUENCE: 13

```
Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
```

```
            20                  25                  30
Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
 50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325

<210> SEQ ID NO 14
<211> LENGTH: 261
<212> TYPE: PRT
<213> ORGANISM: Artificial Sequence
<220> FEATURE:
<223> OTHER INFORMATION: synthetic sequence

<400> SEQUENCE: 14

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
```

-continued

```
                    50                  55                  60
Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

CHIMERIC ENDOCYTIC RECEPTORS AND METHOD OF USE THEREOF

CROSS REFERENCE TO RELATED APPLICATION

This application claims priority under 35 U.S.C. § 119(e) to U.S. Provisional Patent application, Ser. No. 62/919,382, filed Mar. 8, 2019 filed, the disclosures of which are incorporated by reference in its entirety.

FIELD

The invention relates in general to chimeric endocytic receptor (CER)-based constructs and method for using the same for activating and regulating immune response in general, and in particular, relates to a chimeric endocytic receptor (CER) capable of initiating endocytosis of the target antigen and ligand, and genetically engineering T cells with CER (CER-T) or monocytes with CER (CER-M), and the use of the CER-T and CER-M in different disease treatment. Compared to the natural receptor mediated endocytosis, the CER-T present the antigen to initiate immune response or clean the virus or auto-antibody more efficiently. Therefore, such CER-T could be applied in the cellular therapy to treat tumor, viral diseases and autoimmune diseases

SEQUENCE LISTING

An official copy of the sequence listing is submitted concurrently with the specification electronically via EFS-Web as an ASCI I formatted sequence listing with a file name of Sequence_listing_liu_0001US_ST25.txt, a creation date of Mar. 9, 2020, and a size of 12, 146 bytes. The sequence listing contained in this ASCII formatted document is part of the specification and is herein incorporated by reference in its entirety.

BACKGROUND

Endocytosis involves the movement of materials from outside the cell into the cytoplasm. Receptor-mediated endocytosis, a specialized type of endocytosis, is responsible for the uptake of extracellular materials based on receptor ligand binding. This type of endocytosis is associated with the formation of clathrin-coated pits that become clathrin-coated vesicles.

There are several types of natural endocytic receptors, including the Fc receptors for the constant region of immunoglobin G (IgG). There are several different types of Fc receptors (abbreviated FcR), which are classified based on the type of antibody that they recognize. The Latin letter used to identify a type of antibody is converted into the corresponding Greek letter, which is placed after the 'Fc' part of the name. For example, those that bind the most common class of antibody, IgG, are called Fc-gamma receptors (FcγR), those that bind IgA are called Fc-alpha receptors (FcαR) and those that bind IgE are called Fc-epsilon receptors (FcεR). The classes of FcR's are also distinguished by the cells that express them (macrophages, granulocytes, natural killer cells, T and B cells) and the signalling properties of each receptor.

All of the Fcγ receptors (FcγR) belong to the immunoglobulin superfamily and are the most important Fc receptors for inducing phagocytosis of opsonized (marked) microbes. This family includes several members, FcγRI (CD64), FcγRIIA (CD32), FcγRIIB (CD32), FcγRIIIA (CD16a), FcγRIIIB (CD16b), which differ in their antibody affinities due to their different molecular structure. For instance, FcγRI binds to IgG more strongly than FcγRII or FcγRIII does. FcγRI also has an extracellular portion composed of three immunoglobulin (Ig)-like domains, one more domain than FcγRII or FcγRIII has. This property allows FcγRI to bind a sole IgG molecule (or monomer), but it is suggested that all Fcγ receptors must bind multiple IgG molecules within an immune complex to be activated.

Fc receptors of IgG (FcRs) binds to the Fc portion of antibodies to form immune complexes and recruit the complement or the effector system to defend the body against pathogens. Binding of immune complexes to FcR activates effector cells, leading to phagocytosis, endocytosis of IgG-opsonized particles, releases of inflammatory mediators, and antibody-dependent cellular cytotoxicity (ADCC). Fc receptors are found on a number of cells in the immune system including phagocytes like macrophages and monocytes, granulocytes like neutrophils and eosinophils, and lymphocytes of the innate immune system (natural killer cells) or adaptive immune system (e.g., B cells). They allow these cells to bind to antibodies that are attached to the surface of microbes or microbe infected cells, helping these cells to identify and eliminate microbial pathogens. The Fc receptors bind the antibodies at their Fc region (or tail), an interaction that activates the cell that possesses the Fc receptor. Activation of phagocytes is the most common function attributed to Fc receptors. For example, macrophages begin to ingest and kill an IgG-coated pathogen by phagocytosis following engagement of their Fcγ receptors.

FcγRI (CD64), a high-affinity FcRs is constitutively expressed on monocytes, macrophages, eosinophils, and dendritic cells, as well as on neutrophils after activation. FcγRI contains three extracellular Ig-like domains, designated D1, D2, and D3. Earlier mutational analysis suggests that D2 and D3 domains are important to confer high-affinity antibody binding (Hulett and Hogarth, 1998). FcγRI bound to the lower hinge region of the Fc with its D1 and D2 domains resembling the conformation of the two-domain FcγRII, FcγRIII, and FceRI ligand complexes (Radaev et al., 2001; Ramsland et al., 2011; Sondermann et al., 2000). The D3 domain is not in direct contact with Fc in the current complex structure; however, the receptor D3 domain packs against the D2 domain, forming a hydrophobic hinge core, suggesting that the D3 domain is important for maintaining receptor conformation and stability. Most activating receptors are either containing an intracellular immune-receptor tyrosine-based activation motif or associated with an FcR common γ chain (γ chain) (Nimmerjahn and Ravetch, 2008). However, FcγRIIIA and FcγRI are associated with a γ chain that contains an immunoreceptor tyrosine-based activation motif (ITAM sequence) through which signal transduction can proceed (CAMBIER, 1995; ERNST et al., 1993; Groh et al., 2001). The interaction of FcγRI and FcγRIIIA with the γ chain allows these Fcγ receptors, which lack cytoplasmic domain tyrosine crucial for the initiation of signaling cascades, to transmit signals from external stimuli to intracellular molecules. Interaction with the γ chain also plays a role in facilitating cell surface expression of some Fc receptors (Groh et al., 2001). Cell surface expression of FcγRIIIA is not observed in cells obtained from γ chain knockout mice, but expression of FcγRI, while greatly diminished, is detectable in a subset of monocytes/macrophages from γ chain knockout mice (TAKAI et al., 1994). FcγRI transmembrane (TM) domain is important for FcγRI cell surface expression and its interaction with the γ chain. In contrast, that γ chain transmembrane sequences and dimerization of the γ chain are not required for phagocytosis mediated by the γ chain cytoplasmic domain.

Although the cytoplasmic domains of FcγRI contains no known signaling motifs, it could still induce effector functions. The cytosolic domain of FcγRI mediated MHC class II antigen presentation without active FcR γ-chain signaling (van Vugt M J et al., 1999), whereas deletion of FcγRI cytosolic domain retarded kinetics of endocytosis and phagocytosis and abrogated FcγRI-triggered IL-6 secretion (Edberg et al., 1999). FcγRIa-γ-chain complex activation has been documented to involve p72 syk (KIENER et al., 1993) and the Src kinases Lyn (Duchemin and Anderson, 1997) and Hck (WANG et al., 1994) and MAP kinase (DURDEN et al., 1995). Furthermore, serine/threonine phosphorylation of the FcR γ subunit, and in particular Raf 1 activation, couples upstream protein tyrosine kinase activation to downstream signalling events (Park et al., 1996). Interestingly, the Fc receptor γ chain also renders human T cells hyper-responsive to TCR/CD3 stimulation. Overexpression of Fc epsilon RI gamma is associated with increased phosphorylation of Syk kinase, which could subsequently augment TCR-triggered tyrosine phosphorylation of CD3/zeta (Hauck et al., 2015; Nambiar et al., 2003).

Fc gamma receptors belong to the family of Non-catalytic tyrosine-phosphorylated receptors which share a similar signaling pathway involving phosphorylation of tyrosine residues. The receptors generate signals within their cells through an important activation motif known as an Immunoreceptor tyrosine-based activation motif (ITAM). An ITAM is a specific sequence of amino acids (YXXL) occurring twice in close succession in the intracellular tail of a receptor. When phosphate groups are added to the tyrosine (γ) residue of the ITAM by membrane-anchored enzymes of the Src kinase family, a signaling cascade is generated within the cell. This phosphorylation reaction typically follows interaction of an Fc receptor with its ligand. An ITAM is present in the intracellular tail of FcγRIIA, and its phosphorylation induces phagocytosis in macrophages. FcγRI and FcγRIIIA do not have an ITAM but can transmit an activating signal to their phagocytes by interacting with another protein that does. This adaptor protein is called the Fcγ subunit and, like FcγRIIA, contains the two YXXL sequences that are characteristic of an ITAM.

A further need remains for reagents and method of use to treat cancers and other immune system-related disease, which are capable of regulating antigen uptake and presentation in T- and B-cells through nonclassical or alternative mechanisms. In this regard, a chimeric endocytic receptor (CER) might provide great benefit by directly bringing in endocytosis process. However, it is not known whether this concept of CERS can be used to initiate the antigen specific endocytosis and could result in the CER-T present the antigen to initiate/enhance immune response or clean the virus or auto-antibody more efficiently, because it is not a classical pathway for antigen presentation.

SUMMARY

The invention discloses a design of chimeric endocytic receptor (CER) based on the structure of FcγRI/γ chain. An affinity domain from receptors or antibodies is introduced into the endocytic structure of FcγRI/γ chain to form the CER backbone that is capable of uptaking the ligand or antigen specific to the receptors or antibodies. Such design is shown to transform native monocytes or T cells to CER-M or CER-expressing CER-T in recognizing and uptake the target antigen and activate subsequent immune responses. Such engineered CER-M or CER-T could be used to treat tumor, viral diseases and autoimmune diseases directly.

The invention disclosed an alternative or nonclassical construct that activates and modifies specific antigen uptake and presentation in T cells and B cells. In addition to the potential to be used one modality of in combinatorial cell therapy, The FcR-γ-based constructs has the advantage of involving the endocytosis process to enhance and coordinate T cell activation, for example in combination with T cell activation by other types of constructs such as CAR. In addition, CER-T cells may help clean the auto-reactive antibody via inclusion of self-antigen on the cell surface fused to endocytic functional domain that is designed to treat certain autoimmune diseases.

The chimeric endocytic receptor (CER) is capable of initiating endocytosis of the target antigen and ligand, and genetically engineering T cells with CER (CER-T) or monocytes with CER (CER-M), and the use of the CER-T and CER-M in different disease treatment. Compared to the natural receptor mediated endocytosis, the CER-T present the antigen to initiate immune response or clean the virus or auto-antibody more efficiently. Therefore, such CER-T could be applied in the cellular therapy to treat tumor, viral diseases and autoimmune diseases.

The invention disclosed an isolated chimeric endocytic antigen receptor (CER) peptide comprising: an engagement element, a hinge, a human Fc receptor transmembrane and cytoplasmic domain, a 2A self-cleaving peptide, and a Fc receptor gamma chain (FcR-γ), in some embodiments.

The engagement element can be an antibody fragment with high affinity to a target antigen, or an extracellular domain of a receptor, in some embodiments.

The engagement element can be an extracellular domain of a ligand, or a self-antigen, in some embodiments.

The hinge is chosen from the group consisting of IgG1 hinge (SEQ ID NO:1), IgG2 hinge (SEQ ID NO:2), IgG3 hinge (SEQ ID NO:3), and IgG4 hinge (SEQ ID NO:4), in some embodiments.

The Fc receptor is an immunoglobulin Fc receptor selected from FcγRI (CD64), FcγRIIA (CD32), FcγRIIB (CD32), FcγRIIIA (CD16a), and FcγRIIIB (CD16b), in some embodiments.

The Fc receptor transmembrane and cytoplasmic domain comprises FcγRI transmembrane domain (SEQ ID NO:5) and FcγRI cytoplasmic domain (SEQ ID NO:6).

The 2A self-cleaving peptide is at equimolar levels of multiple genes on the same mRNA, and is chosen from T2A (SEQ ID NO:7), P2A (SEQ ID NO:8), E2A (SEQ ID NO: 9), F2A (SEQ ID NO: 10), in some embodiments.

The Fc receptor can be FcR-γ, comprising the amino acid sequence of SEQ ID NO:11, in some embodiments.

The CER peptide further comprises a costimulatory ligand selected from peptide comprising CD80 (SEQ ID NO:12.), CD86 (SEQ ID NO:13.), or CD40L (SEQ ID NO:14), in some embodiments.

The target antigen can be virus associated antigens (VA) selected from virus associated antigens including HPV associated antigen E6/E7, HBV antigen HBs Ag/HBe Ag, EBV antigens EBNA1/LMP1/LMP2/EBER, CMV antigen pp65/pp150/pp52/, HIV antigen p24, RSV, influenza A and B viruses, parainfluenza viruses, adenoviruses, and coronavirus associated antigen S1/S2/N, in some embodiments.

In some embodiments, the target antigen is Tumor associated antigen (TAA), selected from a group consisting of:

(1) Antigens Encoded by Mutated Genes, such as mutated CDK4, CTNNB1, CASP8, P53, KRAS, NRAS, EGFR, EGFRvIII, BRCA1, BRCA2, PALB2, ATM, RAD51D, RECQL, CHEK2, c-MET, (2) Cancer-Germline Genes, such as melanoma-antigen encoding (MAGE), MAGEA/MAGEB/MAGEC, BAGE, GAGE, LAGE/NY-ESO1, SSX genes, (3) Differentiation Genes are derived from proteins that are expressed or overexpressed in a given type of tumor and the corresponding healthy tissue, such as tyrosinase, gp100/pmel17, Melan-A/MART-1, gp75/TRP1, TRP2, CEA, CLL1, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66ae, CD67, CD70, CD70L, CD74, CD79a, CD79b, CD80, CD83, CD95, CD123, CD126, CD132, CD133, CD138, CD147, CD154, gp100, (4) Overexpressed Antigens contributing to tumor growth or metastasis, such as RAGE-1, PRAME, survivin, ERBB2 (HER2/NEU), protein Wilms tumor 1 (WT1), EpCAM, MUC1 (CA15-3), MUC2, MUC3, MUC4, MUC6, MUC16, PMSA, Placental growth factor (PIGF), HIF-1α, EGP-1 (TROP-2), EGP-2, surviving, epidermal glycoprotein 1 (EGP-1, TROP2), EGP-2, FLT3, G250, folate receptor, GAGE, gp100, HLA-DR, CD317 (HM1.24), HMGB-1, (5) Embryonic antigen or fetal antigen or stem cell marker, such as CEA (CEACAM-5), CEACAM-6, AFP, OCT4, CD133, CD90, CD13, c-MET, CDC27, (6) Tumor metastasis associated chemokine receptor: such as CXCR2, CXCR4, CXCR7, CCR5, CCR7, CCR9, CCR10, CX3CR1 (Lazennec G et al., 2010), and (7) Immune suppressive checkpoint protein of PD-L1, VISTA, and Siglec-15.

The ligand or the self-antigen is chosen from the group consisting of insulin, Glutamic Acid Decarboxylase (GAD), and insulinoma-associated protein 2 (IA2), in some embodiments.

A method disclosed for using the peptide described herein, wherein the plasmid DNA, mRNA, lentiviral vector or retroviral vector encoding the CER sequence is used to transduce a human T cell or monocyte or macrophage or B cells or Natural Killer cells to express the CER to treat a cancer, a virus-infected disease or an autoimmune disease.

The invention further discloses an engineered T cell expressing the CER peptide, wherein the cell is selected for the presence of CD3+, CD8+, or CD4+ T markers, in some embodiments.

The invention further discloses an engineered human monocyte expressing the CER peptide, wherein the cell is derived from a donor or an autologous monocyte, in some embodiments.

The CER peptide further comprises a Chimeric Antigen Receptor (CAR), in some embodiments.

The chimeric antigen receptor (CAR) further comprises VH and VL portions of a scFv that targets a TAA, and a hinge of a CD8a hinge or IgG4 hinge, and an intracellular effectors consisting of one or more co-stimulatory signaling domains comprising CD28 intracellular domains (endodomain) or 4-1BB intracellular domain fused to CD37, in some embodiments.

The virus-infected disease is selected from group consisting of a Coronavirus, a SARS-COV, a SARS-COV-2, a MERS, an Ebola, a Cytomegalovirus (CMV), an Epstein-Barr Virus (EBV), a Human Papilloma Virus (HPV), a Human T-Lymphotropic Virus (HTLV), a Cold virus, an Influenza, a Measles, a Mumps, a Rubella, a Polio, an Echo, a Coxsackie, a Hepatitis A, a Hepatitis B, a Hepatitis C, a Rotavirus, a Herpes 1 and 2, a Rabies, a Yellow fever, or a Dengue fever, in some embodiments.

The cancer is selected from a group consisting of a B-lineage acute lymphoblastic leukemia, a B-cell chronic lymphocytic leukemia and a B-cell non-Hodgkin's lymphoma, a lung cancer, a melanoma, a breast cancer, a prostate cancer, a colon cancer, a renal cell carcinoma, a ovarian cancer, a neuroblastoma, a rhabdomyosarcoma, a lymphoma, a acute lymphoblastic leukemia, a small cell lung carcinoma, a Hodgkin's lymphoma, a childhood acute lymphoblastic leukemia, a fibrosarcoma, a myxosarcoma, a liposarcoma, a chondrosarcoma, a osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a pancreatic cancer, a squamous cell carcinoma, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a hepatoma, a bile duct carcinoma, a choriocarcinoma, a seminoma, an embryonal carcinoma, a Wilms' tumor, a cervical cancer, a testicular tumor, a bladder carcinoma, an epithelial carcinoma, a glioma, an astrocytoma, a medulloblastoma, a craniopharyngioma, an ependymoma, a pinealoma, a hemangioblastoma, an acoustic neuroma, a oligodendroglioma, a meningioma, a retinoblastoma, an acute lymphocytic leukemia, an acute myelocytic leukemia, a chronic leukemia, a polycythemia vera, a lymphoma, a multiple myeloma, a Waldenstrom's macroglobulinemia, and a heavy chain disease.

The autoimmune disease is selected from a group consisting of a type 1 diabetes, a rheumatoid arthritis, a systemic lupus erythematosus or an inflammatory bowel disease, in some embodiments.

Still other embodiments will become readily apparent to those skilled in the art from the following detailed description, wherein are described embodiments by way of illustrating the best mode contemplated. As will be realized, other and different embodiments will be possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 1A a CER containing an antibody fragment (such as scFv), a human FcγRI transmembrane and cytoplasmic domain, FcR γ-chain, FIG. 1B a CER containing an extracellular domain of a receptor, the human FcγRI transmembrane and cytoplasmic domain, and the FcR γ-chain, FIG. 1C the CER of (A) with a costimulatory ligand, such as CD86 and/or CD40L, FIG. 1D the CER of FIG. 1B with a costimulatory ligand, such as CD86 and/or CD40L, FIG. 1E the CER of FIG. 1A with a chimeric antigen receptor (CAR); FIG. 1F the CER of FIG. 1B with a CAR.

FIGS. 2A, 2B, 2c, 2D, 2E, and 2F are schematic diagrams showing the structure of the CERs, presented in correspondence to the CERs in FIG. 1. FIG. 2A scFv-Hinge-FcγRI TM/ICD-2A-FcR γ-chain; FIG. 2B Receptor/ligand ED-Hinge-FcγRI TM/ICD-2A-FcR γ-chain; FIG. 2C scFv-Hinge-FcγRI TM/ICD-2A-FcR γ-chain-2A-Costimulatory ligand; FIG. 2D Receptor/ligand ED-Hinge-FcγRI TM/ICD-2A-FcR γ-chain-2A-Costimulatory ligand; FIG. 2E scFv-Hinge-FcγRI TM/ICD-2A-FcR γ-chain-2A-TAA scFv-CD28/41BB-Z; FIG. 2F scFv-Hinge-FcγRI TM/ICD-2A-FcR γ-chain-2A-TAA scFv-CD28/41BB-Z. (TM: transmembrane; ICD: intracellular domain; ED: extracellular domain' 2A: 2A self-cleaving peptide).

FIGS. 5A, 5B, 5C and 5D are cytotoxicity assays examined under fluorescent and B/W microscopes showing CER does not interfere with a CAR-T system's cytotoxicity against tumor cells. HepG2-anti-GPC3-CD28-Z CAR-T cells (FIG. 5C) or anti-AFP CER/anti-GPC3-CD28-Z CAR-T cells (FIG. 5D) were co-cultured with FFluc-GFP cells at E:T ratio=1:10, after 48 h co-culture, the cells were observed under the fluorescence microscope to examine the T cells cytotoxicity against tumors cells. The nontransduced T cells (control)(FIG. 5A) and anti-AFP-CER-T cells (FIG. 5B) were used as negative control. The result indicated anti-AFP CER/anti-GPC3-CD28-Z CAR-T cells could eradicate the HepG2 cells as efficiently as the anti-GPC3-CD28-Z CAR-T cells. Therefore, inclusion of anti-AFP CER design will not interrupt the cytotoxicity of anti-GPC3 CAR-T cells against the tumor cells.

DETAILED DESCRIPTION

Figure 1:
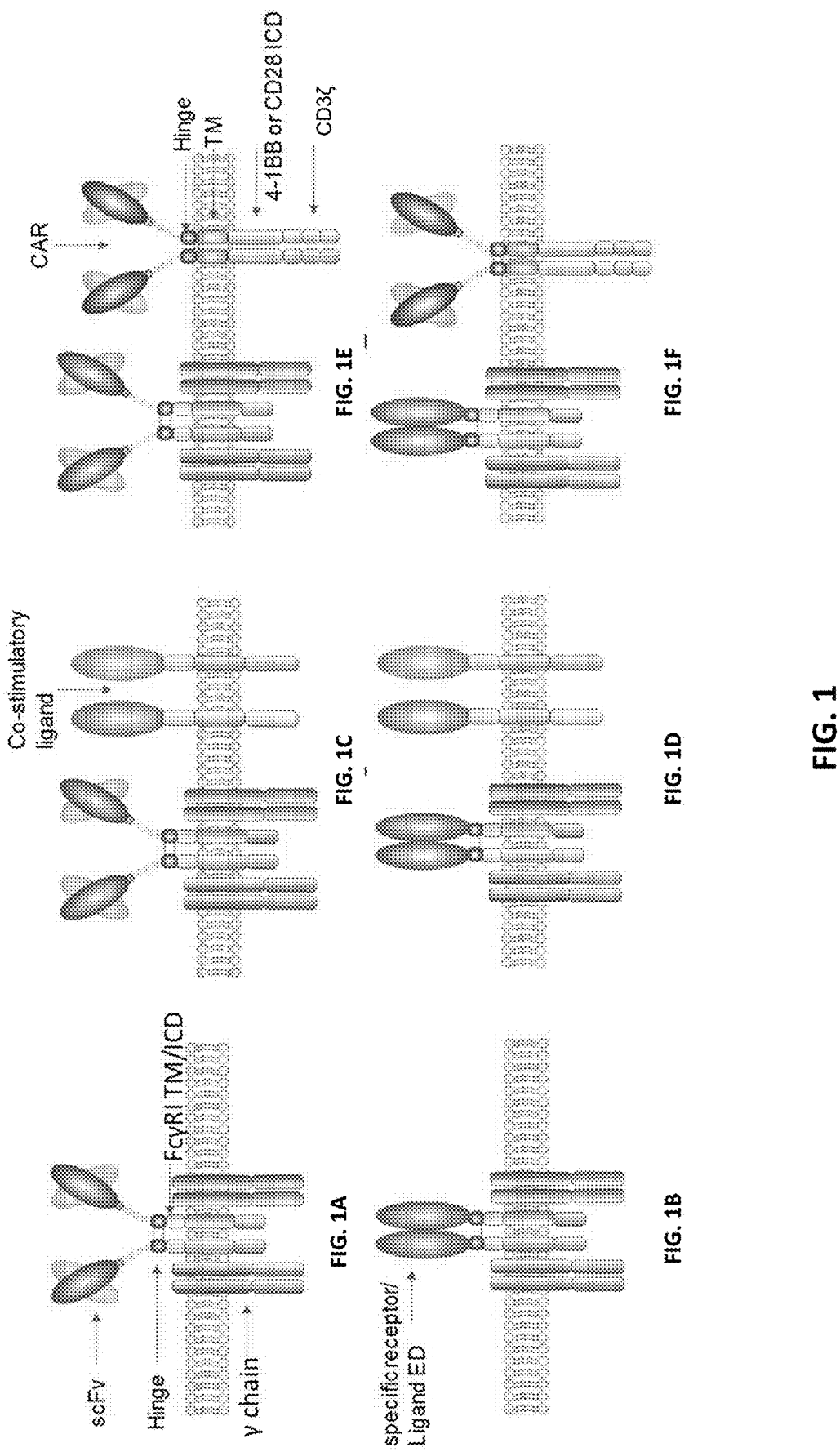
FIGS. 1A, 1B, 1C, 1D, 1E and 1F are schematic illustrations showing CERs structural domains disposed in cell membranes.

Combined with the composition of the test device and the assembly diagram, the working principle and measuring method of the testing device is described in detail in the following. Reference is made to the accompanying drawings in which like references indicates similar elements, and in which is shown by way of illustration, specific embodiments in which the invention may be practiced. These embodiments are described in sufficient detail to enable those skilled in the art to practice the invention. In other instances, well-known circuits, structures, and techniques have not been shown in detail in order not to obscure the understanding of this description. The following detailed description is, therefore, not to be taken in a limiting sense, and the scoop of the invention is defined only by the appended claims.

In one embodiment, a series of CER constructs were made using recombination DNA techniques. The schematic illustrations of the structure domains of these CER constructs are shown in FIGS. 1A, 1B, 1C, 1D, 1E and 1F. (A) shows a CER containing an antibody fragment (such as scFv), a human FcγRI transmembrane and cytoplasmic domain, FcR γ-chain, (B) shows a CER containing an extracellular domain of a receptor, the human FcγRI transmembrane and cytoplasmic domain, and the FcR γ-chain, (C) shows a CER of (A) with a costimulatory ligand, such as CD86 and/or CD40L, (D) The CER of (B) with a costimulatory ligand, such as CD86 and/or CD40L, (E) The CER of (A) with a chimeric antigen receptor (CAR); and (F) The CER of (B) with a CAR.

The antibody fragment (such as scFv) has high affinity to target antigen, which in turn allows specific targeting to target molecules in disease intervention. The extracellular domain of a receptor has high affinity to its ligand, which in turn allows specific targeting of target molecules in disease intervention. Although not shown, the CER constructs may contain a ligand domain instead of a receptor domain, thus targeting a specific receptor. The FcR γ-chain forms a homodimer that further associates with the portions of the endocytic receptor to propagate signaling required for T cell or B cell activation. The CERs constructs may also include costimulatory ligands, such as CD86 and/or CD40L, which provide additional stimulation signaling to T cells or B cells. The CERs may also include a chimeric antigen receptor (CAR), which direct the engineered T cells to tumor sites and display the cytotoxicity against tumor cells.

The structures of the CER constricts are further illustrated in FIGS. 2A-2F. (A) scFv-Hinge-FcγRI TM/ICD-2A-FcR γ-chain; (B) Receptor/ligand ED-Hinge-FcγRI TM/ICD-2A-FcR γ-chain; (C) scFv-Hinge-FcγRI TM/ICD-2A-FcR γ-chain-2A-Costimulatory ligand; (D) Receptor/ligand ED-Hinge-FcγRI TM/ICD-2A-FcR γ-chain-2A-Costimulatory ligand; (E) scFv-Hinge-FcγRI TM/ICD-2A-FcR γ-chain-2A-TAA scFv-CD28/41BB-Z; (F) scFv-Hinge-FcγRI TM/ICD-2A-FcR γ-chain-2A-TAA scFv-CD28/41BB-Z. (TM is an abbreviation for transmembrane; ICD is an abbreviation for intracellular domain; ED is an abbreviation for extracellular domain; 2A refers to a 2A self-cleaving peptide that direct cleavage of synthesized peptides. 2A is chosen from the group of T2A (SEQ ID NO: 7), P2A (SEQ ID NO: 8), E2A (SEQ ID NO: 9), and F2A (SEQ ID NO: 10); Hinge is chosen from the group of IgG1 Hinge (SEQ ID NO: 1), IgG2 Hinge (SEQ ID NO: 2), IgG3 Hinge (SEQ ID NO: 3), and IgG4 Hinge (SEQ ID NO: 4); FcγRI TM refers to a fusion between FcγRI transmembrane domain (SEQ ID NO: 5) and FcγRI cytoplasmic domain (SEQ ID NO: 6); FcR-γ are used interchangeably with FcR common γ chain, FcR γ-chain or γ chain (SEQ ID NO: 11)

In the CER constructs, a antigen-binding domain from antibodies or a ligand-binding domain from receptors (such as scFv or ligand ED) is used as an engagement element to specifically bind to the antigens or the ligands, allowing specific interaction with target antigens or target ligands. In some embodiments, the engagement element can be an antigen or ligand, and targets for the interaction can be antibodies or receptors. The binding or interaction between the antibody-antigen or between the receptor-ligand has sufficient affinity and selectivity to allow specific binding under normal physiological conditions.

The hinge refers to (a) an immunoglobulin hinge sequence or a functional fragment or variant thereof, (b) a type II C-lectin interdomain (stalk) region or a functional fragment or variant thereof, or (c) a cluster of differentiation (CD) molecule stalk region or a functional variant thereof. As used herein, a "wild type immunoglobulin hinge region" refers to amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a hinge region comprises a human IgG hinge region, which can be sequence IgG1 hinge (SEQ ID NO:1), IgG2 hinge (SEQ ID NO:2), IgG3 hinge (SEQ ID NO:3), and IgG4 hinge (SEQ ID NO:4).

Figure 3:
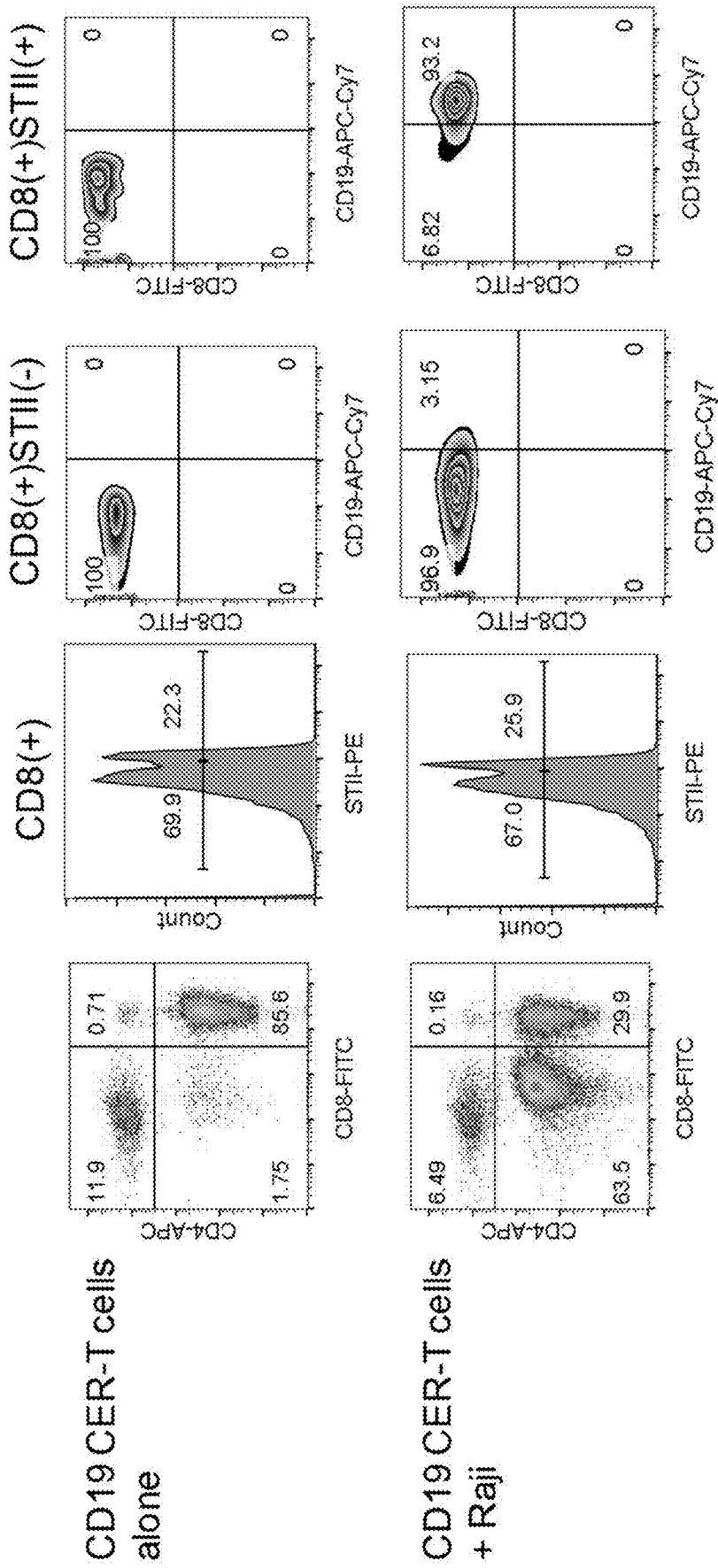
FIG. 3 is a series of flow cytometry profiles showing CER-T cells efficiently capture target antigens on the cell surface.

In one embodiment, the ability of CERs to efficiently capture target antigens is demonstrated, as shown in FIG. 3.

The design of the experiment is as follows: CD19-1ST-CER-T cells were incubated with CD19+ Raji cells for 4 hours, then submitted to flow to detect whether the CER expressed cells could capture the target antigen CD19. The CD19-1ST-CER-T cells alone was used as negative control. The detection of CD19 on the STII (+) CD8+ T cells would indicate that the CER efficiently capture CD19 from Raji cells. An lentiviral construct encoding a chimeric endocytic receptor comprising anti-CD19-scFv (FMC63)-FcγRI-2A-γ was designed, which is composed of Single-Chain Variable Fragment (scFv) derived from the anti-CD 19 specific monoclonal antibody FMC63, the Strep tag II (STII), the FcγRI transmembrane and cytoplasmic domain, 2A, and the γ chain. The DNA encoding the design was cloned into the lentiviral vector (pLenti CMV GFP-puro) and the lentivirus were produced in 293T cells, using the package vectors (psPAX and pMD2G). The selected CD3+ T cells were stimulated by CD3/CD28 microbeads and infected by the lentivirus encoding CD19-scFv (FMC63)-STII-FcγRI-2A-γ, and subsequently expanded in vitro for 12 days. The ability of the CER construct to capture the target antigen CD19 was examined in vitro by coculture with the Raji cells, a CD19+ Burkitt's lymphoma cells line at an effector: target ratio of 1:6. After 4h of incubation, the cells were submitted to flow cytometry. The CER transduced T cells was quantified by the expression the cell surface marker of strep tag II. Compared to the controls with no Raji cells, CD19 was detected on the STII (+) CD8+ T cells, which indicates CD19 CER-T cells captured CD19 from Raji cells efficiently.

The target antigen can be a virus associated antigens (VA), which is selected from the any virus associated antigens, the exemplary virus antigen could be HPV associated antigen E6/E7, HBV antigen HBs Ag/HBe Ag, EBV antigens EBNA1/LMP1/LMP2/EBER, CMV antigen pp65/pp150/pp52/, HIV antigen p24, RSV, influenza A and B viruses, parainfluenza viruses, adenoviruses, coronavirus associated antigen S1/S2/N.

The target antigen can be a TAA, which is selected from the seven groups:

(1) Antigens Encoded by Mutated Genes, such as mutated CDK4, CTNNB1, CASP8, P53, KRAS, NRAS, EGFR, EGFRvIII, BRCA1, BRCA2, PALB2, ATM, RAD51D, RECQL, CHEK2, c-MET, or (2) Cancer-Germline Genes, such as melanoma-antigen encoding (MAGE), MAGEA/MAGEB/MAGEC, BAGE, GAGE, LAGE/NY-ESO1, SSX genes, or (3) Differentiation Genes derived from proteins that are expressed or overexpressed in a given type of tumor and the corresponding healthy tissue, such as tyrosinase, gp100/pmel17, Melan-A/MART-1, gp75/TRP1, TRP2, CEA, CLL1, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66ae, CD67, CD70, CD70L, CD74, CD79a, CD79b, CD80, CD83, CD95, CD123, CD126, CD132, CD133, CD138, CD147, CD154, gp100, or (4) Overexpressed Antigens contributing to tumor growth or metastasis, such as RAGE-1, PRAME, survivin, ERBB2 (HER2/NEU), protein Wilms tumor 1 (WT1), EpCAM, MUC1 (CA15-3), MUC2, MUC3, MUC4, MUC6, MUC16, PMSA, Placental growth factor (PIGF), HIF-1α, EGP-1 (TROP-2), EGP-2, surviving, epidermal glycoprotein 1 (EGP-1, TROP2), EGP-2, FLT3, G250, folate receptor, GAGE, gp100, HLA-DR, CD317 (HM1.24), HMGB-1, or (5) Embryonic antigen or fetal antigen or stem cell marker, such as CEA (CEACAM-5), CEACAM-6, AFP, OCT4, CD133, CD90, CD13, c-MET, CDC27, or (6) Tumor metastasis associated chemokine receptor: such as CXCR2, CXCR4, CXCR7, CCR5, CCR7, CCR9, CCR10, CX3CR1 (Lazennec G et al., 2010), or (7) Immune suppressive checkpoint: PD-L1, VISTA, Siglec-15.

Figure 4:
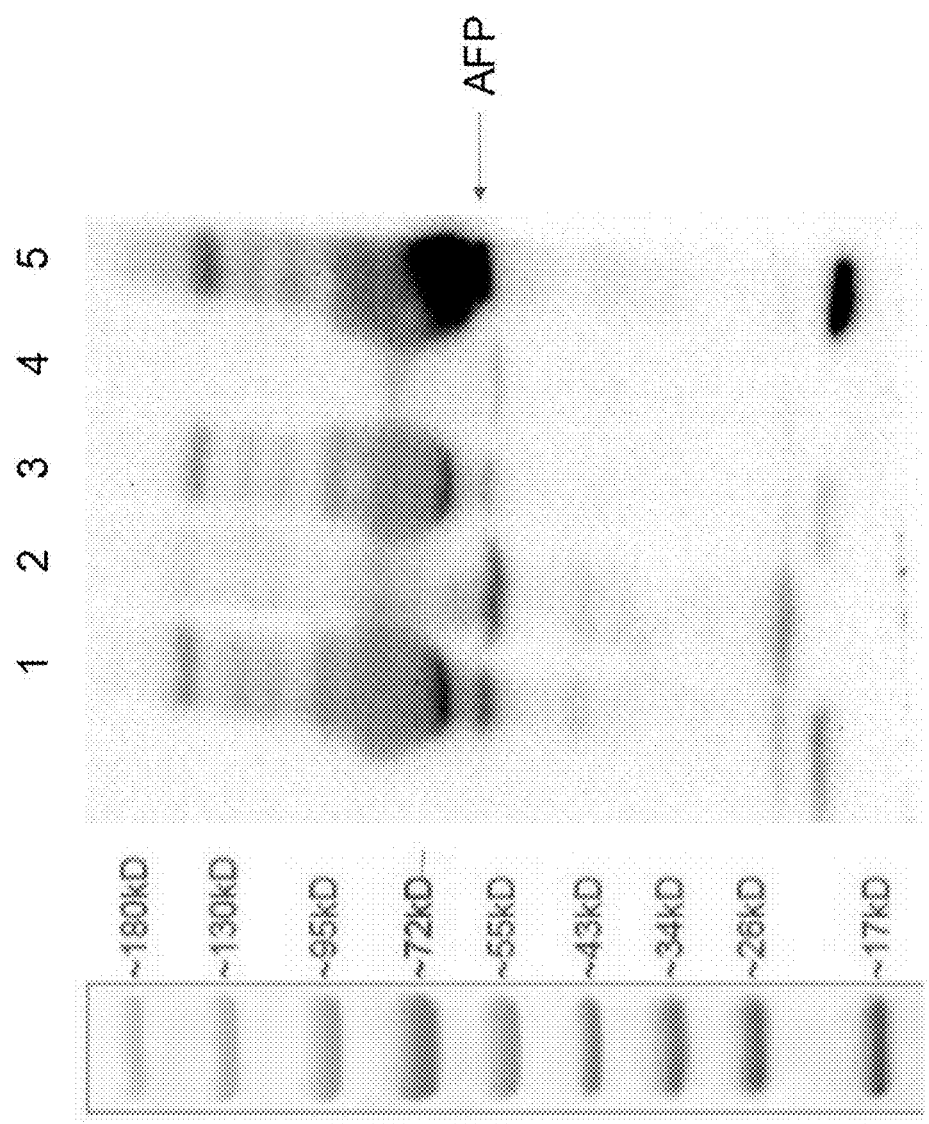
FIG. 4 is a Western blot showing CER-T cells efficiently uptake the target antigen from media into the cells. Lane (1), the HepG2 supernatant after incubation with Anti-AFP-CER-T cells for 12 h; lane (2), the Anti-AFP-CER-T cells after cultured in HepG2 supernatant for 12 h; lane (3), the HepG2 supernatant after incubation with Anti-AFP-CER-T cells for 24 h; lane (4), the Anti-AFP-CER-T cells after cultured in HepG2 supernatant for 24 h; lane (5), the HepG2 supernatant alone. The result indicated anti-AFP CER-T cells efficiently uptake AFP from the supernatant into the cells and degrade the AFP inside the cells. (AFP: alpha fetoprotein).

In one embodiment, CER-T cells efficiently uptake a target antigen from the cell media and degrade the target antigen, as shown in FIG. 4.

An lentiviral construct encoding a chimeric endocytic receptor comprising anti-alpha fetoprotein-scFv-FcγRI-2A-γ was designed, which is composed of Single-Chain Variable Fragment (scFv) derived from the anti-AFP specific monoclonal antibody Immu31 (Qu Z et al., 1999), the FcγRI transmembrane and cytoplasmic domain, 2A, and γ chain. The selected CD3+ T cells were stimulated by CD3/CD28 microbeads and infected by the lentivirus encoding AFP-scFv (Immu31)-STII-FcγRI-2A-γ, and were subsequently expand in vitro for 12 days. Its ability to capture the target alpha fetoprotein was examined in vitro by incubated the AFP CER-T cells with the supernatant derived from the HepG2 cells, which typically secrets AFP into the medium.

As shown in FIG. 4, Anti-AFP-CER-T cells were incubated with the HepG2 cells supernatant which contains AFP for 12 h and 24 h, the supernatant and the Anti-AFP-CER-T cells were submitted to western blotting to examine the AFP uptake by the CER-T cells. Lane (1), the HepG2 supernatant after incubation with Anti-AFP-CER-T cells for 12 h; lane (2), the Anti-AFP-CER-T cells after cultured in HepG2 supernatant for 12 h; lane (3), the HepG2 supernatant after incubation with Anti-AFP-CER-T cells for 24 h; lane (4), the Anti-AFP-CER-T cells after cultured in HepG2 supernatant for 24 h; lane (5), the HepG2 supernatant alone. Compared to lane 5, the AFP level decreased notably in 12 hours and disappeared in 24 hours in T cells expressing the AFP-specific CER constructs. The result indicated anti-AFP CER-T cells efficiently uptake AFP from the supernatant into the cells and degrade the AFP inside the cells. (AFP: alpha fetoprotein).

In one embodiment, CER does not interfere with a CAR-T system's cytotoxicity against tumor cells.

As shown in FIG. 5, a lentiviral construct encoding a chimeric endocytic receptor comprising anti-alpha fetoprotein-scFv-FcγRI-T2A-γ was introduced with anti-GPC3 CAR elements, which includes an anti-GPC3 scFv (Nakano K Y T et al., 2007), IgG4 hinge, CD28 transmembrane and cytoplasmic domain fused CD3 zeta chain. The selected CD3+ T cells were stimulated by CD3/CD28 microbeads and infected by the lentivirus encoding AFP-scFv (Immu31)-STII-FcγRI-T2A-γ-T2A-GPC3-CD28Z, and subsequently expand in vitro for 12 days. To test whether inclusion of CER in the CAR-T design will interrupt the CAR-T cells' cytotoxicity against tumor cells, AFP CER/

GPC3 CAR-T were co-cultured with the HepG2 cells transduced with EGFP, at E:T ratio=1:10. After 48h co-culture, the cells were observed under the fluorescence microscope to examine the AFP CER/GPC3 CAR-T T cells cytotoxicity against HepG2-EGFP cells.

Comparison of (C), (D) versus (A), (B) showed the effective cytotoxic effect ofr the anti-GPC3 CAR system; comparison of (D) versus (C) showed that introduction of CER did not reduce or interrupt the cytotoxicity of the anti-GPC3 CAR system. Thus, the result indicated anti-AFP CER/anti-GPC3-CD28-Z CAR-T cells could eradicate the HepG2 cells as efficiently as the anti-GPC3-CD28-Z CAR-T cells. Therefore, inclusion of the anti-AFP CER design does not interrupt the cytotoxicity of CAR-T cells against the target cells.

In one embodiment, inclusion of a CER in a CAR design enhances the activation of CAR-T cells to kill the target cells.

Figure 6:
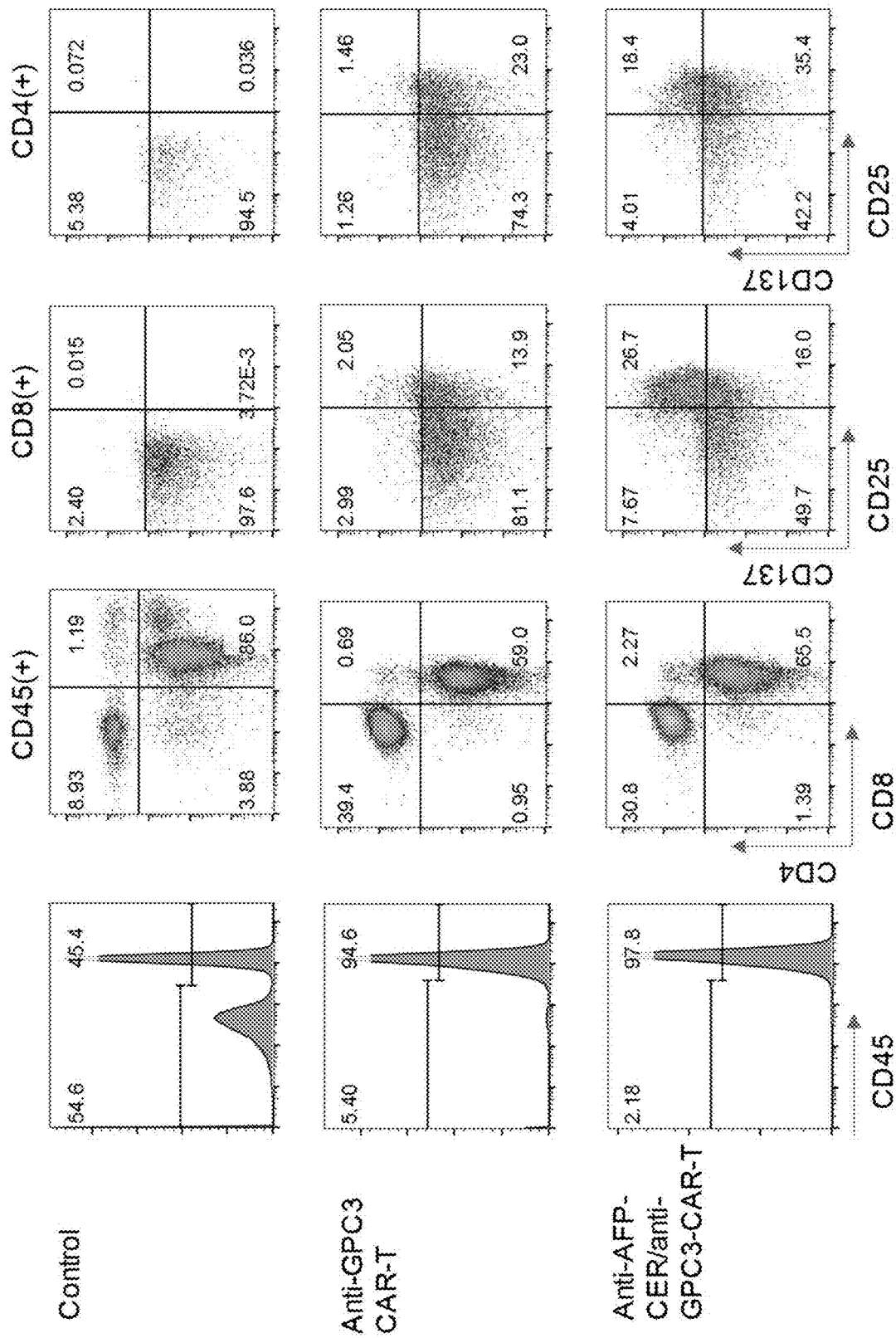
FIG. 6 is a series of flow cytometry profiles showing that CER-constructs enhance the activation of CAR-T cells in killing target cells.

As shown in FIG. 6, Anti-GPC3-CD28-Z CAR-T cells and anti-AFP CER/anti-GPC3-CD28-Z CAR-T cells were co-cultured with HepG2-FFluc-GFP cells at ET ratio=1:5. After 48h co-culture, the cells were submitted to flow cytometry with staining of CD45, CD8, CD4, CD25 and CD137 to examine the T cells activation and cytotoxicity against the tumors cells. The nontransduced T cells (control) were used as negative control. HepG2 cells are CD45 negative and readily distinguished from the CD45+ T cells. Both CD25 and CD137 have been reported to be up-regulated depending on the T-cell stimulus after stimulation, thus can serve indicator of T cell activation (Malek T R et al., 2004; Watts T H. 2005). The result indicated anti-AFP CER/anti-GPC3-CD28-Z CAR-T cells were able to efficiently eradicate HepG2 cells in the co-culture (comparing the three panels in the left column). Moreover, the anti-AFP CER/anti-GPC3-CD28-Z CAR-T cells have notably higher levels of CD25 and CD137 compared to the Anti-GPC3-CD28-Z CAR-T cells (comparing the bottom panel to middle panel in the two right columns in FIG. 6), indicating the inclusion of a CER into a CAR-T system enhances the activation the CAR-T cells. Therefore, inclusion of CER construct enhanced the activation and cytotoxicity of CAR-T cells against the tumor cells.

REFERENCE

Qu Z, Losman M J, Eliassen K C, Hansen H J, Goldenberg D M, Leung S O. Humanization of Immu31, an alpha-fetoprotein-specific antibody. Clin Cancer Res. 1999 October; 5(10 Suppl):3095s-3100s.

Malek T R1, Bayer A L. Tolerance, not immunity, crucially depends on IL-2. Nat Rev Immunol. 2004 September; 4(9):665-74.

Watts TH.TNF/TNFR family members in costimulation of T cell responses. Annu Rev Immunol. 2005; 23:23-68. Review.

CAMBIER, J., 1995, ANTIGEN AND FC RECEPTOR SIGNALING—THE AWESOME POWER OF THE IMMUNORECEPTOR TYROSINE-BASED ACTIVATION MOTIF (ITAM): Journal of Immunology, v. 155, p. 3281-3285.

Duchemin, A., and C. Anderson, 1997, Association of non-receptor protein tyrosine kinases with the Fc gamma RI/gamma-chain complex in monocytic cells: Journal of Immunology, v. 158, p. 865-871.

DURDEN, D., H. KIM, B. CALORE, and Y. LIU, 1995, THE FC-GAMMA-RI RECEPTOR SIGNALS THROUGH THE ACTIVATION OF HCK AND MAP KINASE: Journal of Immunology, v. 154, p. 4039-4047.

Edberg, J., A. Yee, D. Rakshit, D. Chang, J. Gokhale, Z. Indik, A. Schreiber, and R. Kimberly, 1999, The cytoplasmic domain of human Fc gamma RIa alters the functional properties of the Fc gamma RI center dot gamma-chain receptor complex: Journal of Biological Chemistry, v. 274, p. 30328-30333.

ERNST, L., A. DUCHEMIN, and C. ANDERSON, 1993, ASSOCIATION OF THE HIGH-AFFINITY RECEPTOR FOR IGG (FC-GAMMA-RI) WITH THE GAMMA-SUBUNIT OF THE IGE RECEPTOR: Proceedings of the National Academy of Sciences of the United States of America, v. 90, p. 6023-6027.

Groh, V., R. Rhinehart, J. Randolph-Habecker, M. Topp, S. Riddell, and T. Spies, 2001, Costimulation of CD8 alpha beta T cells by NKG2D via engagement by MIC induced on virus-infected cells: Nature Immunology, v. 2, p. 255-260.

Hauck, F., B. Blumenthal, S. Fuchs, C. Lenoir, E. Martin, C. Speckmann, T. Vraetz, W. Mannhardt-Laakmann, N. Lambert, M. Gil, S. Borte, M. Audrain, K. Schwarz, A. Lim, W. Schamel, A. Fischer, S. Ehl, A. Rensing-Ehl, C. Picard, and S. Latour, 2015, SYK expression endows human ZAP70-deficient CD8 T cells with residual TCR signaling: Clinical Immunology, v. 161, p. 103-109.

Hulett, M., and P. Hogarth, 1998, The second and third extracellular domains of Fc gamma RI (CD64) confer the unique high affinity binding of IgG2a: Molecular Immunology, v. 35, p. 989-996.

KIENER, P., B. RANKIN, A. BURKHARDT, G. SCHIEVEN, L. GILLILAND, R. ROWLEY, J. BOLEN, and J. LEDBETTER, 1993, CROSS-LINKING OF FC-GAMMA RECEPTOR-I (FC-GAMMA-RI) AND RECEPTOR-II (FC-GAMMA-RII) ON MONOCYTIC CELLS ACTIVATES A SIGNAL-TRANSDUCTION PATHWAY COMMON TO BOTH FC-RECEPTORS THAT INVOLVES THE STIMULATION OF P72 SYK PROTEIN-TYROSINE KINASE: Journal of Biological Chemistry, v. 268, p. 24442-24448.

Nambiar, M., C. Fisher, A. Kumar, C. Tsokos, V. Warke, and G. Tsokos, 2003, Forced expression of the Fc receptor gamma-chain renders human T cells hyperresponsive to TCR/CD3 stimulation: Journal of Immunology, v. 170, p. 2871-2876.

Nimmerjahn, F., and J. Ravetch, 2008, Fc gamma receptors as regulators of immune responses: Nature Reviews Immunology, v. 8, p. 34-47.

Park, R., Y. Liu, and D. Durden, 1996, A role for Shc, Grb2, and Raf-1 in Fc gamma RI signal relay: Journal of Biological Chemistry, v. 271, p. 13342-13348.

Radaev, S., S. Motyka, W. Fridman, C. Sautes-Fridman, and P. Sun, 2001, The structure of a human type III Fc gamma receptor in complex with Fc: Journal of Biological Chemistry, v. 276, p. 16469-16477.

Ramsland, P., W. Farrugia, T. Bradford, C. Sardjono, S. Esparon, H. Trist, M. Powell, P. Tan, A. Cendron, B. Wines, A. Scott, and P. Hogarth, 2011, Structural Basis for Fc gamma RIIa Recognition of Human IgG and Formation of Inflammatory Signaling Complexes: Journal of Immunology, v. 187, p. 3208-3217.

Sondermann, P., R. Huber, V. Oosthuizen, and U. Jacob, 2000, The 3.2-angstrom crystal structure of the human IgG1 Fc fragment-Fc gamma RIII complex: Nature, v. 406, p. 267-273.

TAKAI, T., M. L I, D. SYLVESTRE, R. CLYNES, and J. RAVETCH, 1994, FCR GAMMA-CHAIN DELETION RESULTS IN PLEIOTROPIC EFFECTOR CELL DEFECTS: Cell, v. 76, p. 519-529.

WANG, A., P. SCHOLL, and R. GEHA, 1994, PHYSICAL AND FUNCTIONAL ASSOCIATION OF THE HIGH-AFFINITY IMMUNOGLOBULIN-G RECEPTOR (FC-GAMMA-RI) WITH THE KINASES HCK AND LYN: Journal of Experimental Medicine, v. 180, p. 1165-1170.

SEQUENCE LISTING

SEQ ID NO: 1
IgG1 Hinge
EPKSCDKTHTCPPCP

SEQ ID NO: 2
IgG2 Hinge
ERKCCVECPPCP

SEQ ID NO: 3
IgG3 Hinge
EPKSCDTPPPCPPCP

SEQ ID NO: 4
IgG4 Hinge
ESKYGPPCPSCP

SEQ ID NO: 5
FcγRI transmembrane domain
LQVLGLQLPTPVWFHVLFYLAVGIMFLVNTVLWVTI

SEQ ID NO: 6
FcγRI cytoplasmic domain
RKELKRKKKWDLEISLDSGHEKKVISSLQEDRHLEEELKCQEQKEEQLQE
GVHRKEPQGAT

SEQ ID NO: 7
T2A
GSGEGRGSLLTCGDVEENPGP

SEQ ID NO: 8
P2A
GSGATNFSLLKQAGDVEENPGP

SEQ ID NO: 9
E2A
GSGQCTNYALLKLAGDVESNPGP

SEQ ID NO: 10
F2A
GSGVKQTLNFDLLKLAGDVESNPGP

SEQ ID NO: 11
FcR-γ
MIPAVVLLLLLLVEQAAALGEPQLCYILDAILFLYGIVLTLLYCRLKIQV
RKAAITSYEKSDGVYTGLSTRNQETYETLKHEKPPQ

SEQ ID NO: 12
CD80 (T-lymphocyte activation antigen CD80 precursor [Homo sapiens]. NP_005182
MGHTRRQGTSPSKCPYLNFFQLLVLAGLSHFCSGVIHVTKEVKEVATLSC
GHNVSVEELAQTRIYWQKEKKMVLTMMSGDMNIWPEYKNRTIFDITNNLS
IVILALRPSDEGTYECVVLKYEKDAFKREHLAEVTLSVKADFPTPSISDF
EIPTSNIRRIICSTSGGFPEPHLSWLENGEELNAINTTVSQDPETELYAV
SSKLDFNMTTNHSFMCLIKYGHLRVNQTFNWNTTKQEHFPDNLLPSWAIT
LISVNGIFVICCLTYCFAPRCRERRRNERLRRESVRPV SEQ ID NO: 13
CD86 (T-lymphocyte activation antigen CD86 isoform 1 precursor [Homo sapiens]. NP_787058
MDPQCTMGLSNILFVMAFLLSGAAPLKIQAYFNETADLPCQFANSQNQSL
SELVVFWQDQENLVLNEVYLGKEKFDSVHSKYMGRTSFDSDSWTLRLHNL
QIIKDKGLYQCIIHHKKPTGMIRIHQMNSELSVLANFSQPEIVPISNITEN
VYINLTCSSIHGYPEPKKMSVLLRTKNSTIEYDGVMQKSQDNVTELYDVS
ISLSVSFPDVTSNMTIFCILETDKTRLLSSPFSIELEDPQPPPDHIPWIT
AVLPTVIICVMVFCLILWKWKKKKRPRNSYKCGTNTMEREESEQTKKREK
IHIPERSDEAQRVFKSSKTSSCDKSDTCF SEQ ID NO: 14
CD40L (CD40 ligand, [Homo sapiens]. NP_000065
MIETYNQTSPRSAATGLPISMKIFMYLLTVFLITQMIGSALFAVYLHRRL
DKIEDERNLHEDFVFMKTIQRCNTGERSLSLLNCEEIKSQFEGFVKDIML
NKEETKKENSFEMQKGDQNPQIAAHVISEASSKTTSVLQWAEKGYYTMSN
NLVTLENGKQLTVKRQGLYYIYAQVTFCSNREASSQAPFIASLCLKSPGR
FERILLRAANTHSSAKPCGQQSIHLGGVFELQPGASVFVNVTDPSQVSHG
TGFTSFGLLKL

What is claimed is:

1. A chimeric endocytic antigen receptor (CER) complex comprising:
   a) a homodimer of a chimeric polypeptide comprising an engagement element and a human Fc receptor transmembrane and cytoplasmic domain, and
   b) two homodimers of Fc receptor gamma chain (FcR-γ), wherein each chimeric polypeptide is associated with one of the homodimers of FcR-γ at the human Fc receptor transmembrane and cytoplasmic domain of the chimeric polypeptide.

2. The complex of claim 1, wherein the engagement element is an antibody fragment with high affinity to a target antigen, or an extracellular domain of a receptor.

3. The complex of claim 2, wherein the target antigen is virus associated antigens (VA) selected from the group consisting of: HPV associated antigen E6/E7, HBV antigen HBs Ag/HBe Ag, EBV antigens EBNA1/LMP1/LMP2/EBER, CMV antigen pp65/pp150/pp52/, HIV antigen p24, RSV, influenza A and B viruses, parainfluenza viruses, adenoviruses, and coronavirus associated antigen S1/S2/N.

4. The complex of claim 2, wherein the target antigen is selected from the group consisting of:
   mutated CDK4, CTNNB1, CASP8, P53, KRAS, NRAS, EGFR, EGFRVIII, BRCA1, BRCA2, PALB2, ATM, RAD51D, RECQL, CHEK2, c-MET,
   melanoma-antigen encoding (MAGE), MAGEA/MAGEB/MAGEC, BAGE, GAGE, LAGE/NY-ESO1, SSX,
   tyrosinase, gp100/pmel17, Melan-A/MART-1, gp75/TRP1, TRP2, CEA, CLL1, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66ae, CD67, CD70, CD70L, CD74, CD79a, CD79b, CD80, CD83, CD95, CD123, CD126, CD132, CD133, CD138, CD147, CD154, gp100,
   RAGE-1, PRAME, survivin, ERBB2 (HER2/NEU), protein Wilms tumor 1 (WT1), EpCAM, MUC1 (CA15-3), MUC2, MUC3, MUC4, MUC6, MUC16, PMSA, Placental growth factor (PIGF), HIF-1a, EGP-1 (TROP-2), EGP-2, survivin, epidermal glycoprotein 1 (EGP-1, TROP2), EGP-2, FLT3, G250, folate receptor, GAGE, gp100, HLA-DR, CD317 (HM1.24), HMGB-1,
   CEA (CEACAM-5), CEACAM-6, AFP, OCT4, CD133, CD90, CD13, c-MET, CDC27,
   CXCR2, CXCR4, CXCR7, CCR5, CCR7, CCR9, CCR10, CX3CR1, PD-L1, VISTA, and Siglec-15.

5. The complex of claim 1, wherein the engagement element is an extracellular domain of a ligand, or a self-antigen.

6. The complex of claim 5, wherein the ligand or the self-antigen is selected from the group consisting of insulin, Glutamic Acid Decarboxylase (GAD), and insulinoma-associated protein 2 (IA2).

7. The complex of claim 1, wherein the chimeric polypeptide further comprises a hinge between the engagement element and the human Fc receptor transmembrane and cytoplasmic domain, wherein the hinge is selected from the group consisting of IgG1 hinge, IgG2 hinge, IgG3 hinge, and IgG4 hinge.

8. The complex of claim 1, wherein the human Fc receptor transmembrane and cytoplasmic domain comprises a transmembrane domain and a cytoplasmic domain of an immunoglobulin Fc receptor selected from the group consisting of: FcγRI (CD64), FcγRIIA (CD32), FcγRIIB (CD32), FcγRIIIA (CD16a), and FcγRIIIB (CD16b).

9. The complex of claim 8, wherein the Fc receptor transmembrane and cytoplasmic domain comprises FcγRI transmembrane domain comprising the amino acid sequence of SEQ ID NO: 5 and FcγRI cytoplasmic domain comprising the amino acid sequence of SEQ ID NO: 6.

10. The complex of claim 1, wherein the FcR-γ comprises the amino acid sequence of SEQ ID NO:11.

11. An engineered T cell expressing the complex of claim 1, wherein the cell further expresses CD3+, CD8+, or CD4+ T cell markers.

12. The complex of claim 1, further comprising a costimulatory ligand selected from the group consisting of: CD80, CD86, or CD40L.

13. The engineered T cell of claim 11, further comprising a Chimeric Antigen Receptor (CAR).

14. The engineered T cell of claim 13, wherein the chimeric antigen receptor (CAR) further comprises heavy chain variable region (VH) and light chain variable region (VL) portions of a single-chain fragment variable (scFv) that targets a tumor associated antigen (TAA); a hinge of a CD8a hinge or IgG4 hinge; and an intracellular effector consisting of one or more co-stimulatory signaling domains comprising CD28 intracellular domains (endodomain) or 4-1BB intracellular domain.

15. An engineered human monocyte expressing the complex of claim 1, wherein the cell is derived from a donor or an autologous monocyte.

16. A chimeric endocytic antigen receptor (CER) polypeptide comprising a chimeric polypeptide comprising an engagement element, and a human Fc receptor transmembrane and cytoplasmic domain, wherein the human Fc receptor transmembrane and cytoplasmic domain is linked to a Fc receptor gamma chain (FcR-γ) via a self-cleavage peptide.

17. The CER polypeptide of claim 16, wherein the self-cleavage peptide is selected from the group consisting of: T2A, P2A, E2A, and F2Z.

* * * * *